Figure 1:
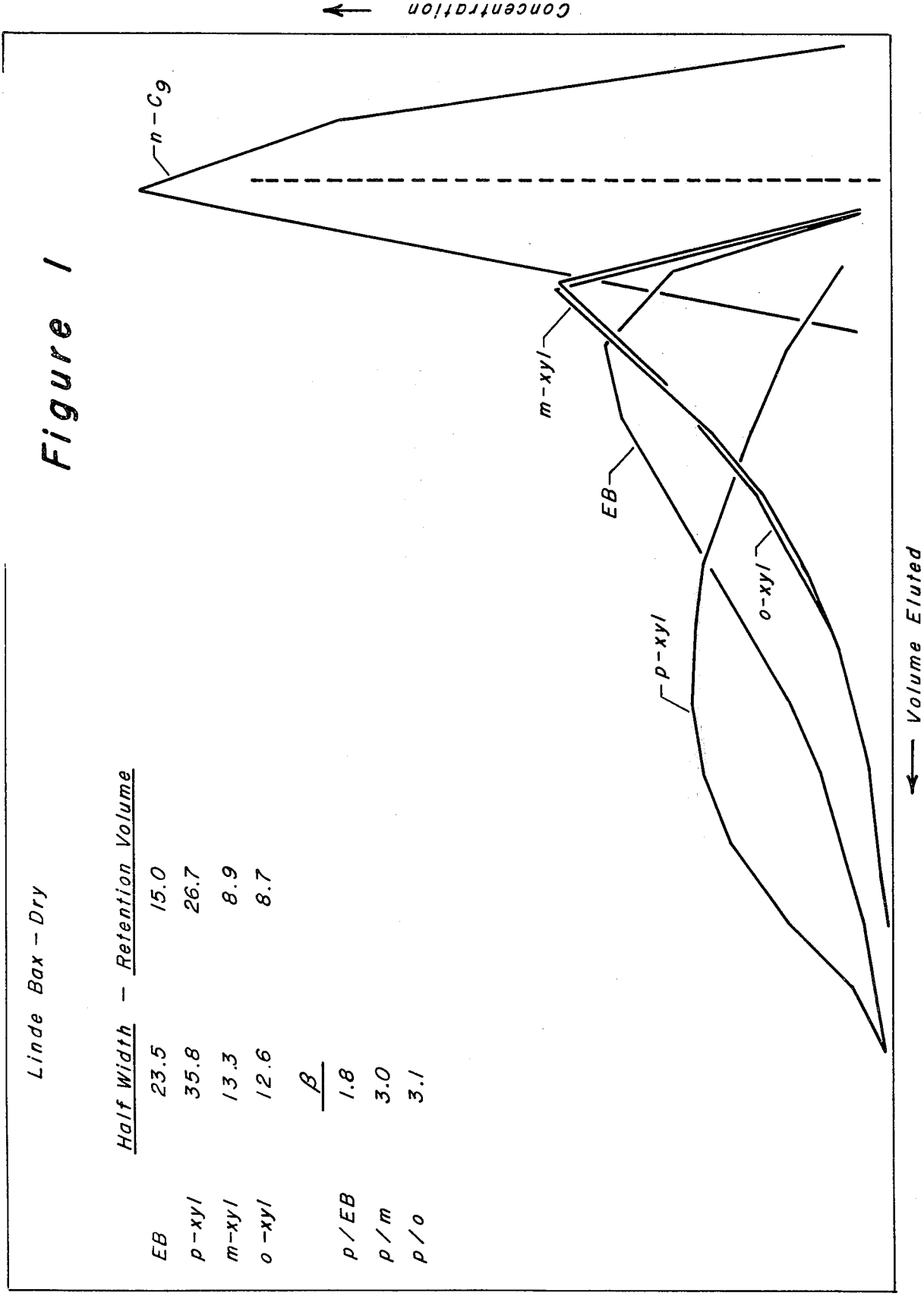

United States Patent [19]

Kulprathipanja

[11] 4,423,279

[45] Dec. 27, 1983

[54] SEPARATION OF BI-ALKYL SUBSTITUTED MONOCYCLIC AROMATIC ISOMERS WITH PYROLYZED ADSORBENT

[75] Inventor: Santi Kulprathipanja, Hoffman Estates, Ill.

[73] Assignee: UOP Inc., Des Plaines, Ill.

[21] Appl. No.: 352,395

[22] Filed: Feb. 25, 1982

[51] Int. Cl.$^3$ .............................................. C07C 7/12
[52] U.S. Cl. ................................................. 585/828
[58] Field of Search ......................................... 585/828

[56] References Cited

U.S. PATENT DOCUMENTS

| | | | |
|---|---|---|---|
| 2,985,589 | 5/1961 | Broughton et al. | 210/34 |
| 3,201,491 | 8/1965 | Stine et al. | 585/821 |
| 3,374,182 | 3/1968 | Young | 252/455 |
| 3,626,020 | 12/1971 | Neuzil | 585/831 |
| 3,663,638 | 5/1972 | Neuzil | 585/831 |
| 3,665,046 | 5/1972 | De Rosset | 585/831 |
| 3,668,266 | 6/1972 | Chen et al. | 585/831 |
| 3,686,343 | 8/1972 | Bearden, Jr. et al. | 585/828 |
| 3,700,744 | 10/1972 | Berger et al. | 585/478 |
| 3,855,333 | 12/1974 | Neuzil | 585/828 |
| 3,894,109 | 7/1975 | Rosback | 585/828 |
| 3,929,669 | 12/1975 | Rosback et al. | 252/455 Z |
| 3,969,223 | 7/1976 | Rosback et al. | 208/310 Z |
| 3,997,620 | 12/1976 | Neuzil | 585/828 |
| 4,048,111 | 9/1977 | Rosback et al. | 252/455 Z |
| 4,283,587 | 8/1981 | Rosback | 585/828 |

*Primary Examiner*—Curtis R. Davis
*Attorney, Agent, or Firm*—James R. Hoatson, Jr.; Louis A. Morris; William H. Page, II

[57] ABSTRACT

A process for the separation of the para-isomer from a hydrocarbon feed mixture comprising at least two bi-alkyl substituted monocyclic aromatic isomers, including the para-isomer, said isomers having from 8 to about 18 carbon atoms per molecule, which process employs an adsorbent comprising a zeolite which has been contacted at pyrolyzing conditions with a pyrolyzing agent to preferentially adsorb the para-isomer. The para-isomer thereafter is removed from the adsorbent by contacting it with a desorbent material and is recovered as a product stream. In a preferred embodiment the process uses a simulated moving-bed countercurrent flow system.

21 Claims, 7 Drawing Figures

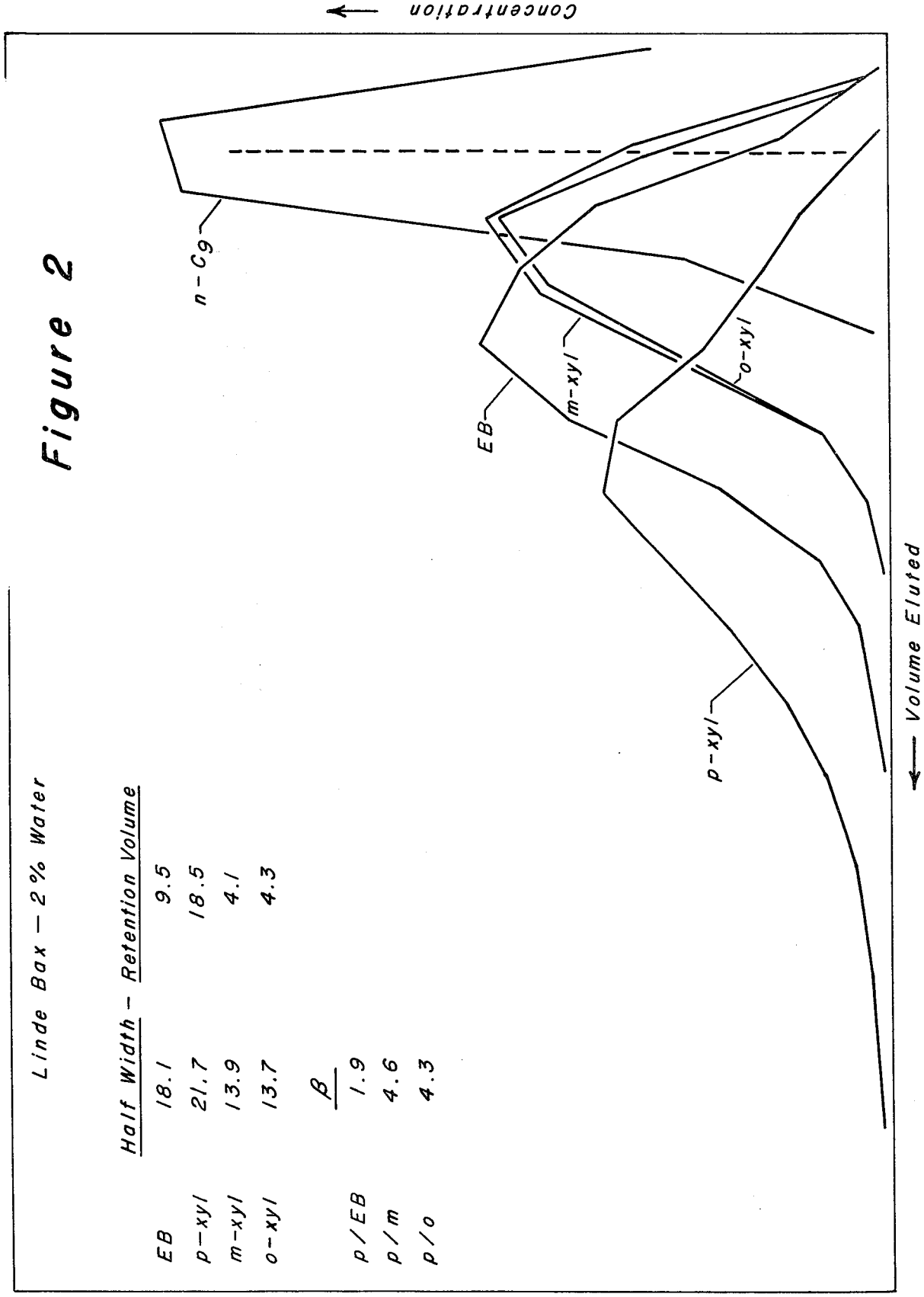

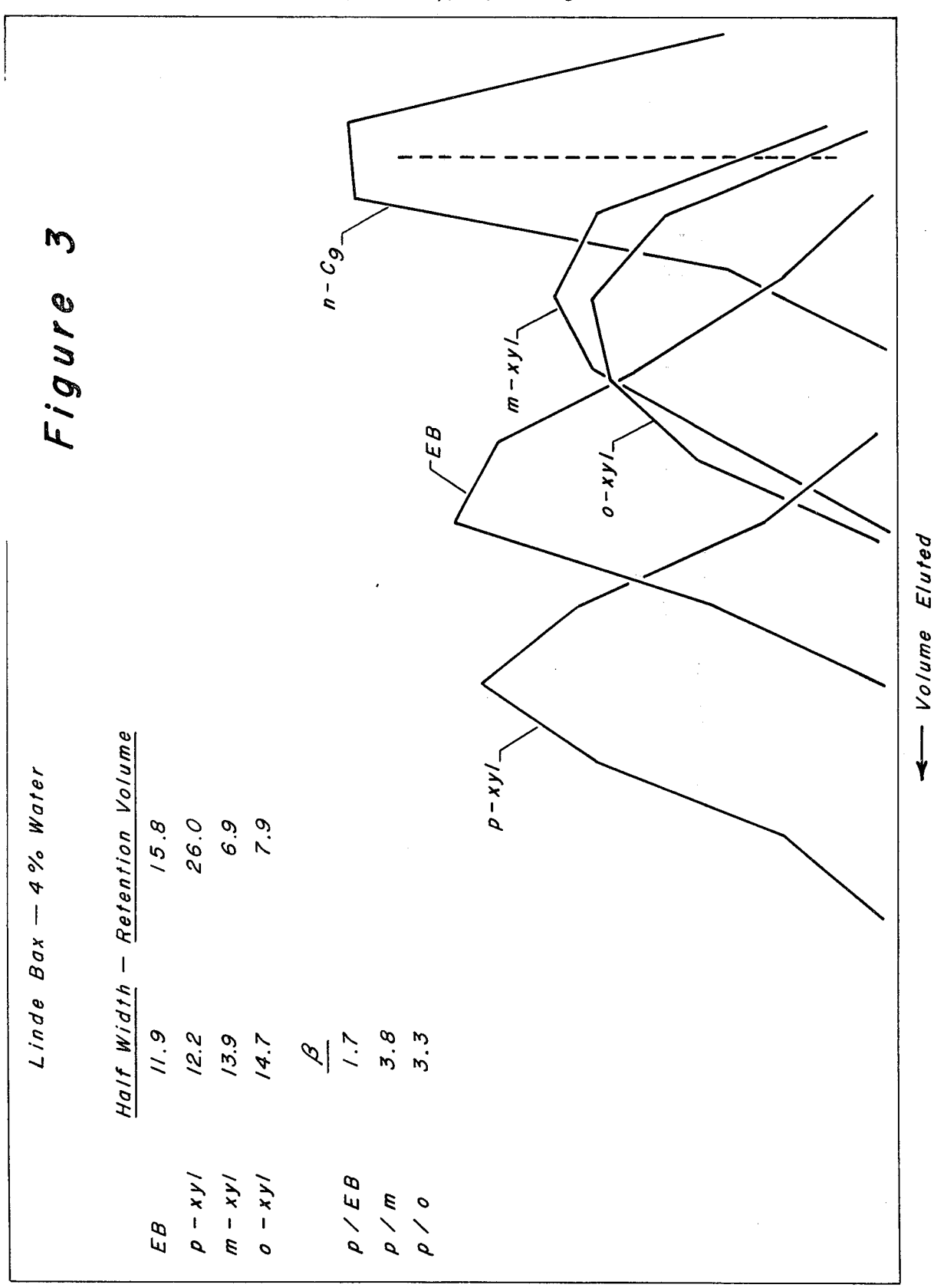

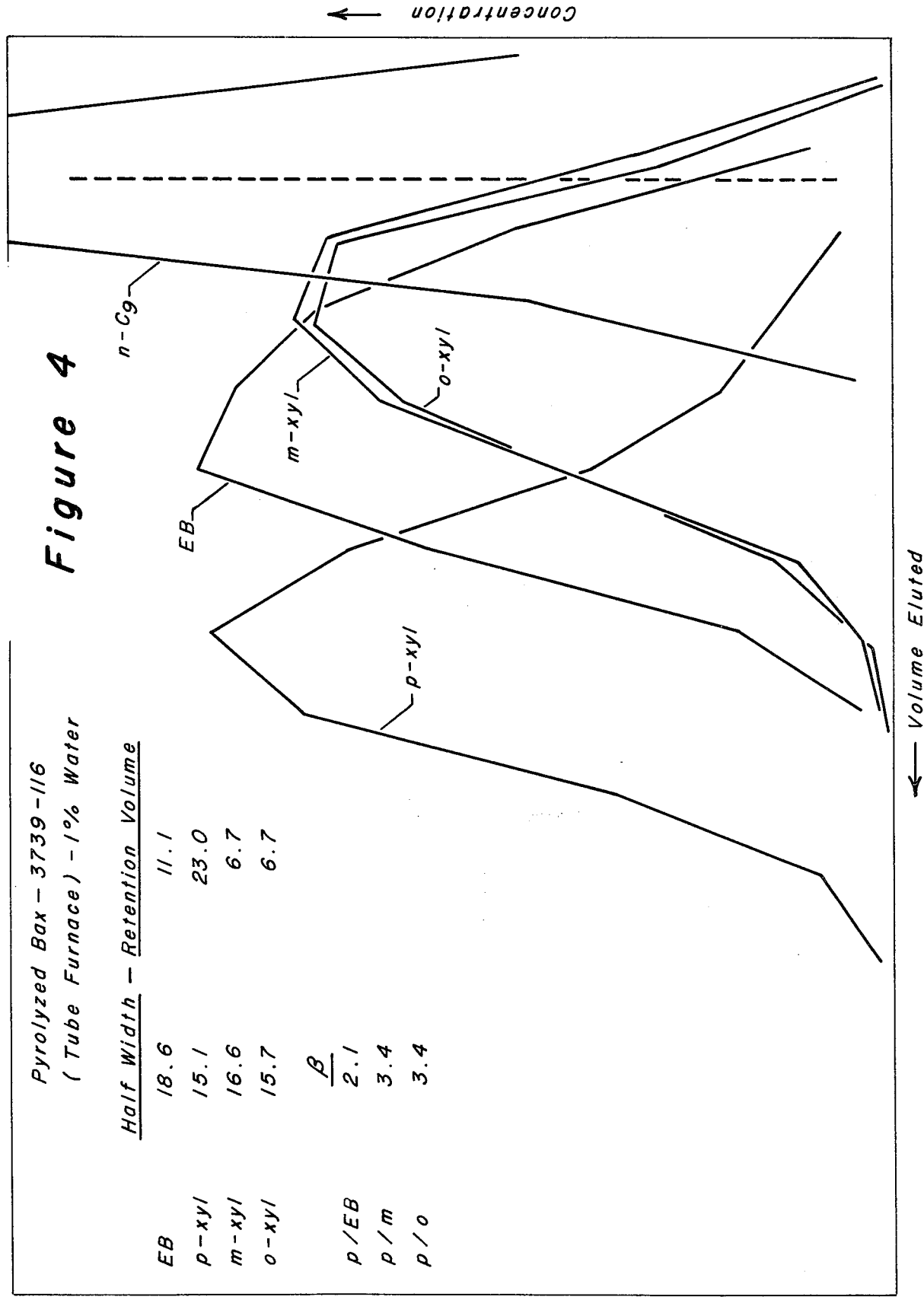

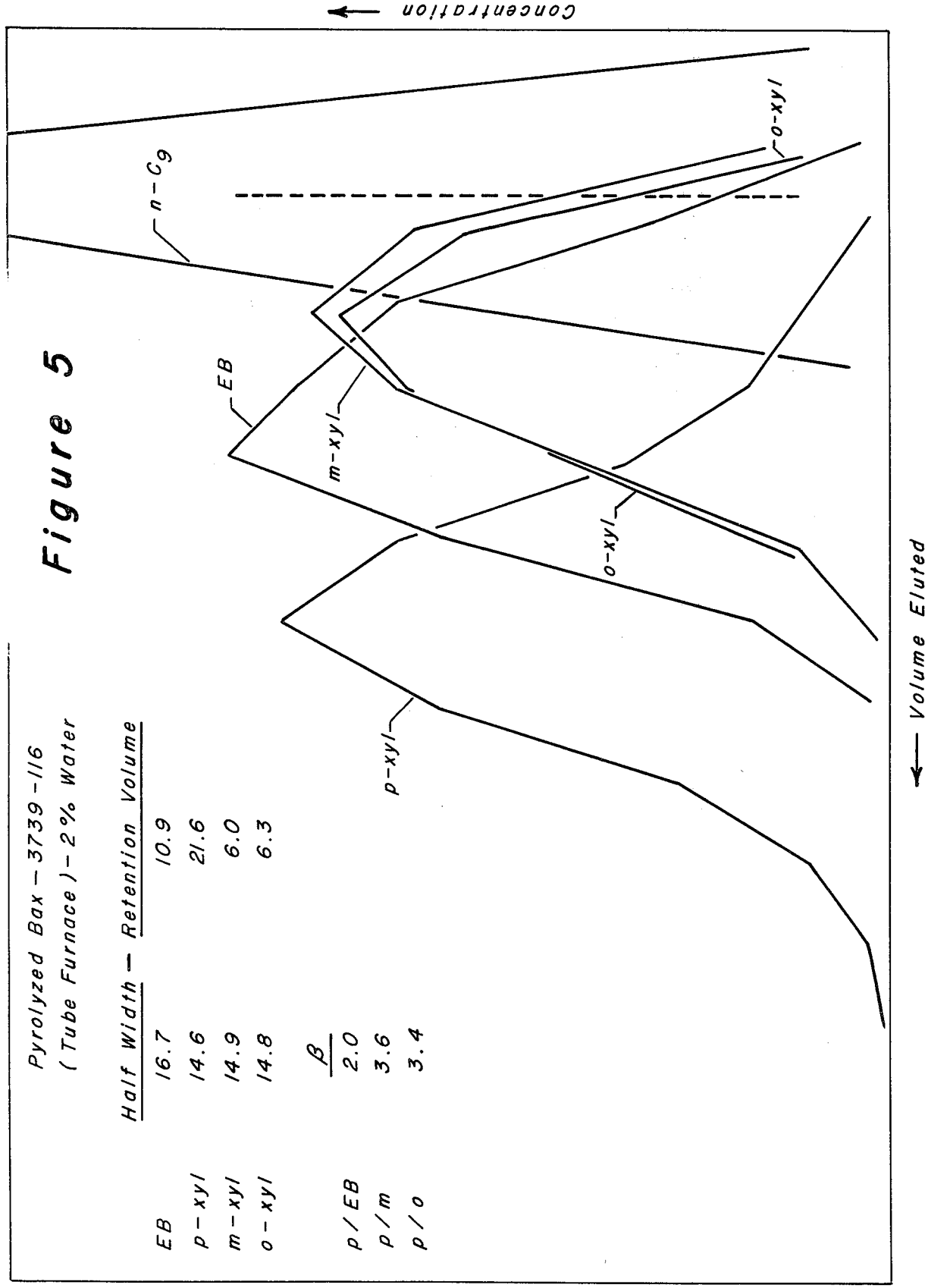

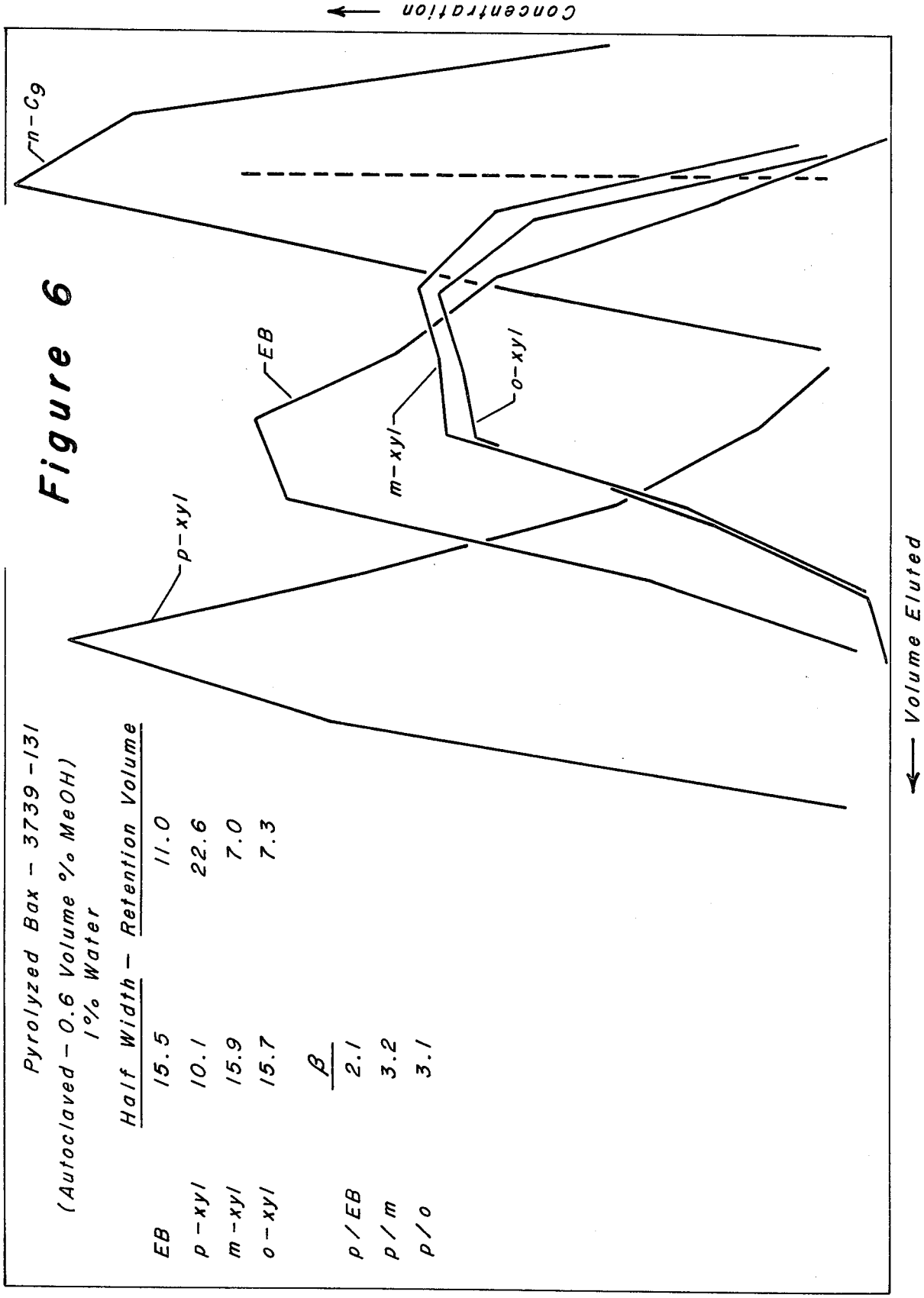

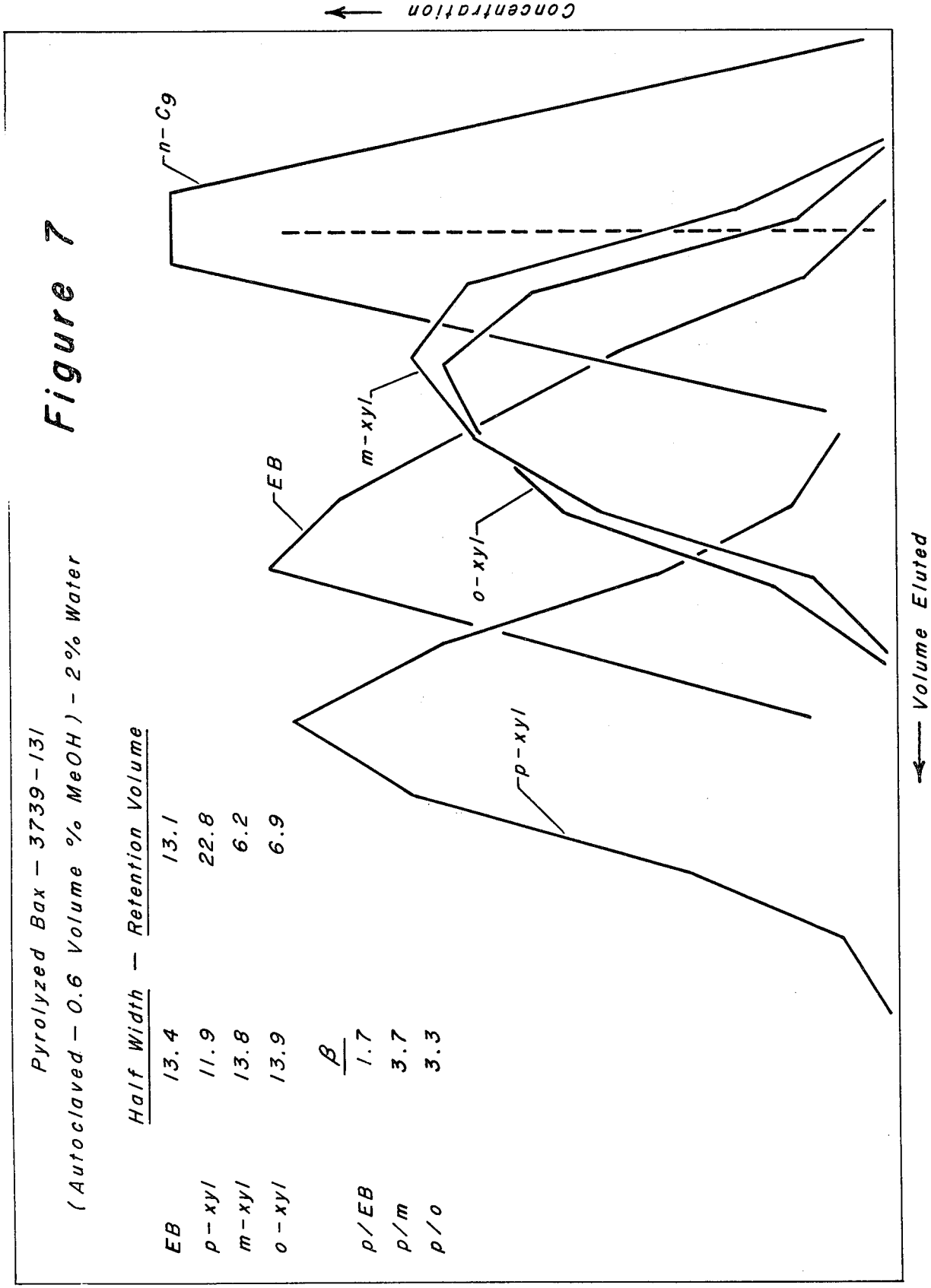

SEPARATION OF BI-ALKYL SUBSTITUTED MONOCYCLIC AROMATIC ISOMERS WITH PYROLYZED ADSORBENT

BACKGROUND OF THE INVENTION

The field of art to which the claimed invention pertains is hydrocarbon separation. More specifically, the invention relates to a process for separating a para-isomer from a feed mixture comprising at least two bi-alkyl substituted monocyclic aromatic isomers, including the para-isomer, the isomers having from 8 to about 18 carbon atoms per molecule which process employs a particular zeolitic adsorbent and a particular flow scheme to selectively remove and subsequently recover the para-isomer from the feed.

DESCRIPTION OF THE PRIOR ART

It is well known in the separation art that certain crystalline aluminosilicates can be used to separate one hydrocarbon type from another hydrocarbon type. The separation of normal paraffins from branched chain paraffins, for example, can be accomplished by using a type A zeolite which has pore openings from 3 to about 5 Angstroms. Such a separation process is disclosed in U.S. Pat. No. 2,985,589 to Broughton et al, and No. 3,201,491 to Stine. These adsorbents allow a separation based on the physical size differences in the molecules by allowing the smaller or normal hydrocarbons to be passed into the cavities within the zeolitic adsorbent, while excluding the larger or branched chain molecules.

In addition to being used in processes for separating hydrocarbon types, adsorbents comprising type X or Y zeolite have also been employed in processes to separate individual hydrocarbon isomers. In the processes described, for example, in U.S. Pat. Nos. 3,626,020 to Neuzil, 3,663,638 to Neuzil, 3,665,046 to deRosset, 3,668,266 to Chen et al, 3,686,343 to Bearden Jr. et al, 3,700,744 to Berger et al, 3,894,109 to Rosback and 3,997,620 to Neuzil, particular zeolitic adsorbents are used to separate para-xylene from other xylene isomers. It is also known that the adsorptive capacity of certain zeolites for certain separations is improved by contacting the zeolite with an aqueous caustic solution. In U.S. Pat. No. 3,374,182 to Young, for example, zeolites so treated are said to be effective in separating aromatic hydrocarbons from non-aromatic hydrocarbons of the same molecular size. In U.S. Pat. Nos. 3,929,669, 3,969,223, and 4,048,111 to Rosback et al these treated zeolites are said to be useful for separating olefins from paraffins.

The present process relates to a process for the separation of the para-isomer from a hydrocarbon feed mixture comprising at least two bi-alkyl substituted monocyclic aromatic isomers, including the para-isomer, the isomers having from 8 to about 18 carbon atoms per molecule. I have found that adsorbents comprising zeolites which have been pyrolyzed at the appropriate conditions exhibit improved selectivity for the para-isomer in such a feed mixture and possess other desired characteristics thereby achieving improved separation of the para-isomer by solid-bed selective adsorption processes. The process is particularly useful in separating para-xylene from feed mixtures containing para-xylene and other xylene isomers.

SUMMARY OF THE INVENTION

In brief summary the present invention is, in one embodiment, a process for separating the para-isomer from a feed mixture comprising at least two bi-alkyl substituted monocyclic aromatic isomers, including the para-isomer, the isomers having from 8 to about 18 carbon atoms per molecule, which process comprises contacting at adsorption conditions the feed with an adsorbent comprising a zeolite which has been pyrolyzed at pyrolyzing conditions with a pyrolyzing agent to effect the adsorption of the para-isomer and thereafter recovering the para-isomer.

In another embodiment, the present invention is a process for separating the para-isomer from a feed mixture comprising at least two bi-alkyl monosubstituted aromatic isomers, including the paraisomer, the isomers having from 8 to about 18 carbon atoms per molecule which process employs an adsorbent comprising a zeolite which has been pyrolyzed at pyrolyzing conditions with a pyrolyzing agent which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones: (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed stream into the adsorption zone at adsorption conditions to effect the selective adsorption of the para-isomer by the adsorbent in the adsorption zone and withdrawing a raffinate output stream from the adsorption zone; (f) passing a desorbent material having a boiling point different than that of the feed mixture to permit separation therefrom by distillation into the desorption zone at desorption conditions to effect the displacement of the para-isomer from the adsorbent in the desorption zone; (g) withdrawing an extract stream comprising the para-isomer and desorbent material from the desorption zone; and (h) periodically advancing through the column of adsorbent in a downstream direction with respect to fluid flow in the adsorption zone, the feed input stream, raffinate output stream, desorbent input stream, and extract output stream to effect the shifting of zones through the adsorbent and the production of extract output and raffinate output streams.

Other embodiments of the present invention encompass details about feed mixtures, adsorbents, desorbent materials, flow schemes and operating conditions all of which are hereinafter disclosed in the following discussion of each of the facets of the present invention.

DESCRIPTION OF THE INVENTION

At the outset the definitions of various terms used throughout this specification will be useful in making clear the operation, objects and advantages of the process.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound, such as an aromatic isomer, that is more selectively adsorbed by the adsorbent while a "raffinate component" is a compound or type of compound that is less selectively adsorbed. In this process, the para-isomer is the extract component and one or more other aromatic isomers is a raffinate component. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the absorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific component, both appearing in the particular stream. For example, the ratio of concentration of the more selectively adsorbed para-isomer to the concentration of less selectively adsorbed meta-isomer will be highest in the extract stream, next highest in the feed mixture, and lowest in the raffinate stream. Likewise, the ratio of the less selectively adsorbed meta-isomer to the more selectively adsorbed para-isomer will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent. When adsorbent "passes" into an operational zone (which zones are used in a preferred embodiment of this process and are hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed mixture components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise at least two bi-alkyl substituted monocyclic aromatic isomers. These isomers can be characterized by reference to Formula 1 below:

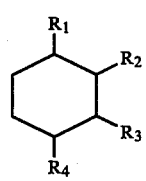

Formula 1 wherein $R_1$, $R_2$, $R_3$ and $R_4$ are selected from the group of alkyl chains and positioned in a manner to provide bi-alkyl substitution at either ortho-, meta-, or para-isomer positions. The R substitutional groups can include alkyl groups ranging from methyl substitution groups up to and including chains having 11 or less carbon atoms per chain. The alkyl side chains can be both normal and branched in nature and are preferably saturated chains.

Thus feed mixtures to this process can contain such specific representative compounds as the various isomers of methylethylbenzene, diethylbenzene, isopropyltoluene (cymene), the methylpropylbenzenes, ethylpropylbenzenes, methylbutylbenzenes, ethylbutylbenzene, dipropylbenzenes, methylpentylbenzene, etc., and combinations thereof. The above list only represents a small fraction of compounds whose isomers can be separated by the adsorptive-separation process of this invention. Thus the process of this invention will be used for example to separate para-methylethylbenzene from a feed mixture comprising para-methylethylbenzene and at least one other methylethylbenzene isomer; para-diethylbenzene from a feed mixture comprising para-diethylbenzene and at least one other diethylbenzene isomer; and para-cymene from a feed mixture comprising para-cymene and at least one other cymene isomer to name a few. The most likely separation for employment of the present invention, however, is the separation of para-xylene from other xylene isomers and ethylbenzene.

The isomers of such compounds are separated by this adsorbent according to their configuration depending whether they are of a para-, meta-, or ortho-isomer construction. Specifically, the para-isomer is selectively adsorbed relative to the other isomers. It is contemplated that when feed mixtures contain more than one homolog of isomers (for example, $C_9$ isomers in mixture with $C_{10}$ or $C_{11}$ isomers) molecular weight differences may unduly interfere with selective adsorption based upon isomer configuration differences. It is therefore preferred that feed mixtures to be separated by this process contain only a single class of aromatic isomers, that is, aromatic isomers having an equal number of carbon atoms per molecule. It is preferable that the isomers have as their only differences the location of the alkyl substituted groups in a para-, meta-, or ortho-position. The alkyl structures should preferably be the same for each isomer of a class. In some instances an isomer may have alkyl chains which are both normal or branched or one branched and one normal.

The feed mixtures may contain small quantities of straight or branched chain paraffins, cycloparaffins, or olefinic material. It is preferable to have these quantities at a minimum amount in order to prevent contamination of products from this process by materials which are not selectively adsorbed or separated by the adsorbent. Preferably the above-mentioned contaminants should be less than about 20% of the volume of the feed mixture passed into the process.

To separate the para-isomer from a feed mixture containing para-isomer and at least one other aromatic isomer the mixture is contacted with the particular adsorbent and the para-isomer is more selectively adsorbed and retained by the adsorbent while the other isomers are relatively unadsorbed and are removed from the interstitial void spaces between the particles of adsorbent and the surface of the adsorbent. The adsorbent containing the more selectively adsorbed para-isomer is referred to as a "rich" adsorbent—rich in the more selectively adsorbed para-isomer. The para-isomer is then recovered from the rich adsorbent by contacting the rich adsorbent with a desorbent material.

The desorbent materials which can be used in this process will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to insure liquid phase, the desorbent material relied upon must be judiciously selected to satisfy several criteria. First the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity to the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, it has been found that desorbent materials comprising monoaromatic hydrocarbons having average boiling points substantially different from that of a feed mixture meet these requirements and are particularly effective. Especially preferred for this process are desorbent materials comprising toluene or diethylbenzene. Usually one of these preferred desorbent materials or the other can be employed with a particular feed mixture such that the requirement of substantially different average boiling points is met. Obviously the desorbent material will not comprise diethylbenzenes when a feed mixture to be separated comprises diethylbenzenes. When the desorbent material comprises diethylbenzene it is preferred that the desorbent material contain only para-diethylbenzene and no other diethylbenzene isomer. Typical concentrations of para-diethylbenzene when para-diethylbenzene is the sole diethylbenzene isomer present in the desorbent material can range from a few volume percent up to about 100 volume percent. More preferably the para-diethylbenzene concentration will be from about 50 to about 75 vol.% of the desorbent material. Diethylbenzene-containing desorbent materials can also comprise mixed diethylbenzenes, one of which will contain roughly about 60 vol.% meta-diethylbenzene, 7 vol.% ortho-diethylbenzene, and 26 vol.% para-diethylbenzene along with approximately 7 vol.% of butylbenzenes. Mixtures comprising toluene or diethylbenzene (either para-diethylbenzene or mixed diethylbenzenes) and diluents are also effective as desorbent materials. Such diluents must be compatible with the adsorbent and feed mixture as described above and must be easily separable from the feed mixture. Diluents which can be used include materials such as saturated hydrocarbons, including paraffins and cycloparaffins and additionally the carbo-cyclic ring compounds. Typically, the paraffins will be straight or branched-chain paraffins having from about 5 to about 20 carbon atoms per molecule and more preferably from about 5 to about 15 carbon atoms per molecule. Cycloparaffins can include the cyclohexane, cyclopentanes, and branched derivatives thereof. Additionally, carbo-cyclic ring compounds including Decalin and Decalin derivatives containing branched chains can be utilized. Typical concentrations of either toluene or diethylbenzene in such mixtures can be from a few volume percent up to near 100 vol.% of the total desorbent material mixture but such concentrations preferably will be within the range of from about 50 vol.% to about 100 vol.% of the mixture.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer (n-nonane for instance) and of the particular aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the peak envelope of the tracer component of some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of specific aromatic isomers is apparently dependent on differences in electrochemical attraction of the different isomers and the adsorbent rather than on pure physical size differences in the isomer molecules.

In hydrated form, the crystalline aluminosilicates generally encompass those zeolites represented by the Formula 1a below:

Formula 1a $$M_{2/n}O:Al_2O_3:wSiO_2:yH_2O$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio is $2.5\pm0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is therefore referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominately sodium. The type Y zeolite containing predominately sodium cations at the exchangeable cationic sites is therefore referred to as a sodium-type Y zeolite.

Cations occupying exchangeable cationic sites in the zeolite may be replaced with other cations by ion exchange methods generally known to those having ordinary skill in the field of crystalline aluminosilicates.

Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed and dried to a desired water content. By such methods the sodium cations and any non-sodium cations which might be occupying exchangeable sites as impurities in a sodium-type X or sodium-type Y zeolite can be partially or essentially completely replaced with other cations.

The term "base material" as used herein shall refer to a material containing an X or a Y zeolite and amorphous material which can be used to make the adsorbents used in my process. The zeolite will typically be present in the base material in amounts ranging from about 75 wt.% to about 98 wt.% of the base material based on volatile free composition. Volatile free compositions are generally determined after the base material has been calcined at 900° C. in order to drive off all volatile matter. The remainder of the base material will generally be amorphous material such as silica, alumina or silicaalumina mixtures or compounds, such as clays, which material is present in intimate mixture with the small particles of the zeolite material. This amorphous material may be an adjunct of the manufacturing process for X or Y zeolite (for example, intentionally incomplete purification of either zeolite during its manufacture) or it may be added to relatively pure X or Y zeolite but in either case its usual purpose is as a binder to aid in forming or agglomerating the hard crystalline particles of the zeolite. Normally the base material will be in the form of particles such as extrudates, aggregates, tablets, macrospheres or granules having a desired particle size range. The adsorbent used in this process will preferably have a particle size range of about 16–60 mesh (Standard U.S. Mesh). Examples of suitable base materials which can be used to make the adsorbents employed in my process are "Molecular Sieves 13X" and "SK-40" both of which are available from Union Carbide Linde Division. The first material of course contains X zeolite while the latter material contains Y zeolite.

It is essential to the present invention that the adsorbent, prior to use, be contacted at pyrolyzing conditions with a pyrolyzing agent. Basically, pyrolyzing comprises the addition to the adsorbent of certain of the products of decomposition of a pyrolyzing agent. The most preferred pyrolyzing agent is an organic solvent containing, preferably, from 1 to 5 carbon atoms per molecule. It is the carbon or carbonaceous material from the decomposed solvent that is incorporated into the adsorbent and which causes the desired effect, i.e. a clear separation of the para-isomer in the feed stream with little or no contamination of a substantial portion of the para-isomer with quantities of other components (tailings) of the feed stream. Preferred pyrolyzing conditions comprise a temperature from about 200° C. to about 800° C. and a contact time of from about 2 hours to about 10 hours.

Without being limited to any theory, it is presumed that the material from the pyrolyzing agent that is incorporated into the adsorbent has a masking effect on certain undesirable components in the adsorbent that cause tailing, particularly amorphous silica. It has been observed that water seems to have a similar masking effect, i.e. the performance of commercial adsorbents may be improved (tailing effect minimized) by adding 4 wt.% or more water thereto, but the water must be continuously replenished because it tends to leave the adsorbent with (and contaminates) the products. The pyrolyzing method of the present invention, however, achieves the same desired effect as water addition without the undesirable side effects, i.e. the pyrolysis products incorporated into the adsorbent do not require replenishment nor do they contaminate the process product streams.

Preferred pyrolyzing conditions comprise a substantially oxygen free environment, a temperature from about 200° C. to about 800° C. and a contact time of from about 2 hours to about 10 hours with the pyrolyzing agent comprising an organic solvent containing from 1 to 5 carbon atoms per molecule. The pyrolyzation may take place in a furnace at atmospheric pressure or in a sealed autoclave, with the oxygen free environment being obtained in either case by purging with an inert gas. When an autoclave is used the volume percentage of liquid pyrolyzing agent to adsorbent required is from about 0.5 to about 1.0, assuming an adsorbent particle size of from about 20 to about 40 mesh. With a furnace the volume percentage of liquid pyrolyzing agent to adsorbent (also comprising from about 20 to about 40 mesh particle size) required is from about 5.0 to about 25.0 with unreacted pyrolyzing agent being recirculated through the furnace in a carrier stream comprising an inert gas. The autoclave clearly makes more efficient use of the pyrolyzing agent by keeping it in close confinement under pressure with the adsorbent. It has been observed, however, both with regard to the tube furnace and autoclave, that too much pyrolyzing agent, e.g. as high as 2 vol.% with the autoclave, will completely nullify the ability of the adsorbent to effect separation.

It has been found that an adsorbent comprising an X zeolite containing at exchangeable cationic sites barium cations satisfies the selectivity requirements and other adsorbent requirements previously discussed and are therefore preferred for use in this process. Adsorbents for this process may be prepared by essentially completely ionexchanging sodium-type X base material, in a particle size range of from about 20 to about 40 U.S. mesh, with the above-mentioned selected cation. Typically the ion exchanges will be done with aqueous solutions of the soluble salts, such as the chlorides, of the respective metal. The term "essentially complete" shall mean that the residual sodium content of the adsorbent after the ion exchange of the base material shall be less than about 2 wt.% $Na_2O$. After ion-exchange and water wash to remove excess ion exchange solution, the adsorbent will be dried to reduce the water content as measured by loss on ignition (LOI) at 900° C. to less than about 10 wt.% and more preferably within a range of from about 1 to about 2 wt.%. Maintaining adsorbent water content within this range is necessary to maintain optimum adsorbent and process performance and water may be added to or removed from the process during operations as necessary to maintain this range. By knowing the initial water content of the adsorbent and by analyzing the process input and output streams for water content, the water content of the absorbent during process operation can be calculated. Water may be added to the adsorbent if necessary either on an intermittent or more preferably on a continuous basis by itself or in admixture with feed or desorbent material to maintain the desired concentration of water on the adsorbent. Water may be removed from the adsorbent if necessary by passing a very dry feed stream to the process and allowing the output streams to remove some water from the adsorbent until the desired range is achieved. The above water content required in the adsorbent of the present invention is considerably less than the known art adsorbents which require at least 4 wt.% water for xylene isomer separation. Less water content in the adsorbent is advantageous from the standpoint of less water contamination of the product.

The adsorbent may be employed in the form a dense fixed bed which is alternatively contacted with a feed mixture and a desorbent material in which case the process will be only semicontinuous. In another embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. In a preferred embodiment therefore the process will use such flow systems. In a more preferred embodiment the process will employ a simulated moving-bed countercurrent flow system. The operating principles and sequence of operation of one such simulated moving-bed countercurrent flow system are described in U.S. Pat. No. 2,985,589 incorporated herein by reference. In such a system it is the progressive movement of multiple liquid access points down an adsorbent chamber that simulates the upward movement of an adsorbent contained in the chamber. Only four of the access lines are active at any one time: the feed input stream, desorbent inlet stream, raffinate outlet stream, and extract outlet stream access lines. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the desired operations to take place although in some instances an optional fourth zone may be used.

The adsorption zone, zone 1, is defined as the adsorbent located between a feed inlet stream and a raffinate outlet stream. In this zone, a feed mixture contacts an adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between an extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 (hereinafter described) into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between a desorbent inlet stream and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating the extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of an adsorbent than some other operational zone. For instance, in some operations the buffer zone can contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an adsorbent be located in a single column which is divided into zones, and the use of multiple chambers or a series of columns is also within the scope of this embodiment.

It is not necessary that all of the input or output streams be simultaneously used, and in fact, in many instances some of the streams can be shut off while others effect an input or output of material. One apparatus which can be utilized to effect the process of this invention in a preferred embodiment will contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations function intermittently as a conduit through which material passes into or out of the process.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol.% and more preferably less than about 1 vol.%. The separation means will typically be a fractionation column, the design and operation of which is well known to the separation art.

Reference can be made to D. B. Broughton U.S. Pat. No. 2,985,589 and to a paper entitled "Continuous Adsorptive Processing—A New Separation Technique" By D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 100° C. to about 200° C. being more preferred and a pressure range of from about atmospheric to about 500 psig with from about atmospheric to about 250 psig being more preferred to insure liquid phase. Desorption conditions will include the same range of temperatures and pressure as used for adsorption conditions.

The size of the units which can utilize the process of this invention can vary anywhere from those of pilot-plane scale (see for example U.S. Pat. No. 3,706,812) to those of commercial scale and can range in flow rates from as little as a few cc an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment a pulse test was performed to evaluate a prior art adsorbent's ability to separate xylene isomers and ethylbenzene. The base material contained a Linde type X structured zeolite and a small portion of amorphous binder material. It was ion-exchanged with barium to give an adsorbent which contained less than about 1 wt.% residual sodium as $Na_2O$. The adsorbent was dried to essentially complete dryness before it was utilized in the process.

The testing apparatus was an adsorbent chamber containing approximately 70 cc of the adsorbent and contained with a temperature-controlled means in order to maintain essentially isothermal operations through the column. For each pulse test the column was maintained at a temperature of 150° C. and a pressure of 100 psig to maintain liquid-phase operations. Gas chromatographic analysis equipment was attached to the column effluent stream in order to determine the composition of the effluent material at given time intervals. The feed mixture employed for each test contained about 5 vol.% each of the xylene isomers and ethylbenzene, 5 vol.% normal nonane which was used as a tracer and 75 vol.% desorbent material. The desorbent material was para-diethylbenzene and n-heptane in a respective ratio of 3 to 7. The operations taking place for each test were as follows. The desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a 10-minute interval at a rate of 1.0 cc per minute. The desorbent stream was then resumed at 1 LHSV and continued to pass into the adsorbent column until all of the feed aromatics had been eluted from the column as determined by observing the chromatograph generated by the effluent material leaving the adsorption column. The sequence of operations usually takes about an hour. The 10 minute pulse of feed and subsequent desorption may be repeated in sequence as often as is desired. The attached FIG. 1 comprises the chromatographic traces for the aromatics and tracer eluted from the column. Selected information derived from these traces is indicated on each attached figure. In particular, the selectivity for p-xylene relative to ethylbenzene (1.8) should be noted, since ethylbenzene, as can be seen from the curves, is the second (after p-xylene) most strongly retained component from the feed mixture, and would, therefore, be the most likely contaminant of the p-xylene product.

The curves in FIG. 1 show a very poor separation achieved for the adsorbent used. Almost all of the p-xylene eluted was contaminated with substantial quantities (tailings) of the other components, particularly with ethylbenzene.

EXAMPLE II

The experiment of Example I was repeated, except that the Linde Ba X adsorbent used contained 2 wt.% water. The results are shown in FIG. II. The water addition clearly helped the adsorbent performance from the standpoint of selectivity and extent of tailings. The quality of the separation and yield of pure product was, however, still poor.

EXAMPLE III

The experiment of Example I was repeated, except that the Linda Ba X adsorbent used contained 4 wt.% water. The results are shown in FIG. III. The additional water added resulted in a marked improvement in the selectivity of the adsorbent for p-xylene and yield of substantially pure p-xylene.

It should be recognized, however, that the higher the adsorbent water content, the greater the water contamination of the aromatic product, in fact the adsorbent water content to product water contamination relationship is greater than linear. The water does not remain indefinitely on the adsorbent, but is carried away by the product and, then, must be continuously replenished.

EXAMPLE IV

The experiment of Example I was repeated, except that the Linda Ba X adsorbent was treated in accordance with the present invention, i.e. the adsorbent was pyrolyzed in a tube furnace with methanol as a pyrolyzing agent in an amount comprising about 11 vol.% of the pyrolyzation reaction mixture and at 400° C. for 4 hours. The adsorbent was dried to 1 wt.% water content. The results are shown in FIG. IV.

It can be seen in FIG. IV that the present invention effects a great improvement in the performance of an adsorbent with regard to selectivity and a reduction in the amount of tailings as compared to a conventional adsorbent with even twice the water content as shown in FIG. II.

EXAMPLE V

The experiment of Example I was repeated, except that the adsorbent was treated in accordance with the present invention as in Example IV and that the water content of the adsorbent was 2 wt.%. The results are shown in FIG. V.

The separation shown in FIG. V is, again, very good and in fact at least as good as that accomplished by the conventional adsorbent of FIG. III which contained 4 wt.% water. The implication of that fact is that water contamination of the product may be minimized by means of the present invention, without sacrifice of separation quality or efficiency.

EXAMPLE VI

The experiment of Example V was repeated, except that the pyrolyzation of the adsorbent was in accordance with the embodiment of the present invention wherein an autoclave is utilized. The pyrolyzing agent (methanol) comprised 0.6 vol.% of the pyrolyzation reaction mixture. The adsorbent was dried to 1 wt.% water. The results are shown in FIG. VI.

The excellent separation shown in FIG. VI was the best obtained thus far in view of the relatively high percentage of p-xylene eluted free of any tailings of any other xylene isomer or ethylbenzene.

EXAMPLE VII

The experiment of Example VI was repeated, except that the adsorbent was dried to a water content of 2 wt.%.

The separation shown in FIG. VII was also excellent, however, not significantly, if at all, better than the separation of Example VI which used adsorbent with one-half the water content.

The present invention, therefore, achieves excellent separations and at the same time minimization of the undesirable presence of water.

I claim as my invention:

1. A process for separating a para-isomer from a feed mixture comprising at least two bi-alkyl substituted monocyclic aromatic isomers, including the para-isomer, said isomers having from 8 to about 18 carbon atoms per molecule, which process comprises contacting at adsorption conditions said feed with an adsorbent comprising a zeolite which has been contacted at pyrolyzing conditions comprising a substantially oxygen-free environment at a temperature of from about 200° C. to about 800° C. for a period of contact time comprising from about 2 hours to about 10 hours with a pyrolyzing agent comprising an organic solvent containing from 1 to 5 carbon atoms to effect the adsorption of the para-isomer and thereafter recovering the para-isomer.

2. The process of claim 1 wherein said para-isomer is para-xylene and said feed mixture comprises para-xylene and at least one other xylene isomer.

3. The process of claim 2 wherein said feed mixture contains ethylbenzene.

4. The process of claim 1 wherein the particle size of said adsorbent is from about 20 to about 40 mesh and said contacting of said adsorbent with said pyrolyzing agent is effected in a sealed autoclave with the volume percentage of liquid pyrolyzing agent to adsorbent of from about 0.5 to about 1.0.

5. The process of claim 1 wherein the particle size of said adsorbent is from about 20 to about 40 mesh and said contacting of adsorbent with said pyrolyzing agent is effected in a furnace at atmospheric pressure with a volume percentage of liquid pyrolyzing agent to adsorbent of from about 5.0 to about 25.0 with vaporized, unreacted pyrolyzing agent being recirculated through said furnace in a carrier stream comprising an inert gas.

6. The process of claim 1 wherein cations occupying exchangeable cationic sites in the zeolite of the precursor of said adsorbent are exchanged with other cations.

7. The process of claim 6 wherein said other cations comprise cations of barium.

8. The process of claim 7 wherein said zeolite comprises a type X zeolite.

9. The process of claim 1 wherein said adsorbent contains from about 1 wt.% to about 2 wt.% water.

10. The process of claim 1 wherein said adsorption conditions include a temperature within the range of from about 20° C. to about 250° C. and a pressure within the range of from about atmospheric to about 500 psig to ensure liquid phase.

11. A process for separating the para-isomer from a feed mixture comprising at least two bi-alkyl monosubstituted aromatic isomers, including the para-isomer, said isomers having from 8 to about 18 carbon atoms per molecule which process employs an adsorbent comprising a zeolite which has been contacted at pyrolyzing conditions comprising a substantially oxygen-free environment at a temperature of from about 200° C. to about 800° C. for a period of contact time comprising from about 2 hours to about 10 hours with a pyrolyzing agent comprising an organic solvent containing from 1 to 5 carbon atoms, which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed stream into said adsorption zone at adsorption conditions to effect the selective adsorption of said para-isomer by said adsorbent in said adsorption zone and withdrawing a raffinate output stream from said adsorption zone;

(f) passing a desorbent material having a boiling point different than that of the feed mixture to permit separation therefrom by distillation into said desorption zone at desorption conditions to effect the displacement of said para-isomer from the adsorbent in said desorption zone;

(g) withdrawing an extract stream comprising said para-isomer and desorbent material from said desorption zone;

(h) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

12. The process of claim 11 wherein said para-isomer is para-xylene and said feed mixture comprises para-xylene and at least one other xylene isomer.

13. The process of claim 12 wherein said feed mixture contains ethylbenzene.

14. The process of claim 11 wherein the particle size of said adsorbent is from about 20 to about 40 mesh and said contacting of said adsorbent with said pyrolyzing agent is effected in a sealed autoclave with the volume percentage of liquid pyrolyzing agent to adsorbent of from about 0.5 to about 1.0.

15. The process of claim 11 wherein the particle size of said adsorbent is from about 20 to about 40 mesh and said contacting of adsorbent with said pyrolyzing agent is effected in a furnace at atmospheric pressure with a volume percentage of liquid pyrolyzing agent to adsorbent of from about 5.0 to about 25.0 with vaporized, unreacted pyrolyzing agent being recirculated through said furnace in a carrier stream comprising an inert gas.

16. The process of claim 9 wherein cations occupying exchangeable cationic sites in the zeolite of the precursor of said adsorbent are exchanged with other cations to obtain said adsorbent.

17. The process of claim 16 wherein said other cations comprise cations of barium.

18. The process of claim 9 wherein said zeolite comprises a type X zeolite.

19. The process of claim 11 wherein said adsorbent contains from about 1 wt.% to about 2 wt.% water.

20. The process of claim 11 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

21. The process of claim 11 further characterized in that said adsorption conditions and desorption conditions include a temperature within the range of from about 20° C. to about 250° C. and a pressure within the range of from about atmospheric to about 500 psig to ensure liquid phase.

* * * * *